United States Patent [19]

Chomant et al.

[11] Patent Number: 5,126,122
[45] Date of Patent: Jun. 30, 1992

[54] RADIOLABELED HYALURONECTIN COMPOSITION FOR THE DIAGNOSIS AND/OR TREATMENT OF CANCER

[75] Inventors: Jean Chomant, Malaunay; Marie-Noelle Courel, Rouen; Bertrand Delpech, Saint-Aubin-Les-Elbeuf; Nicole Girard, Rouen, all of France

[73] Assignee: University de Rouen, Mont-Saint-Aigan, France

[21] Appl. No.: 562,238

[22] Filed: Aug. 3, 1990

[30] Foreign Application Priority Data

Aug. 8, 1989 [FR] France .................. 89 10797

[51] Int. Cl.⁵ .............. A61K 49/02; A61K 43/00
[52] U.S. Cl. ............................ 424/1.1; 252/645
[58] Field of Search ................. 424/1.1; 252/645

[56] References Cited

U.S. PATENT DOCUMENTS

| | | | |
|---|---|---|---|
| 4,746,504 | 5/1988 | Nimrod et al. | 424/1.1 |
| 5,015,577 | 5/1991 | Weigel et al. | 435/101 |
| 5,019,498 | 5/1991 | Chichibu | 435/7.5 |

Primary Examiner—John S. Maples

[57] ABSTRACT

This composition is made up of an injectable aqueous solution of a glycoprotein, hyalurenectin, onto which a radioactive element is bound.

9 Claims, No Drawings

RADIOLABELED HYALURONECTIN COMPOSITION FOR THE DIAGNOSIS AND/OR TREATMENT OF CANCER

The object of this invention is the use, for diagnostic and/or treatment purposes, of cancer in particular, with a specific glycoprotein, namely hyaluronectin.

We are aware of the difficulties related to the diagnosis and the treatment of cancer, and the importance of developing an effective method of diagnosis allowing for treatment of the disease as early as possible.

A scintigraphic method has already been proposed for this purpose, making use of monoclonal antibodies charged with radioactive isotopes. Still, the problems linked to this method are many -- on the one hand, the relatively weak affinity of the monoclonal antibodies to the cancerous antigens, and on the other hand, their strictly specific nature vis-a-vis said antigens, and lastly, the inevitable immunological reactions of the human body to antibodies coming from animals, most often mice. To these problems we can add the one created by the fact that the antigen which fixes its antibodies is not always represented in the cancerous metastases, but only in the original tumor, such that this method does not permit location of all of the cancerous sites in an organism with certainty.

We are thus faced with the problem of developing a method which does not involve any of the aforementioned problems, and which allows for accurate and complete diagnosis, permitting location of all of the cancerous sites in a human body, without a risk of immunological reaction.

The purpose of this invention is to offer a solution to the problem thus posed, by proposing a diagnostic method which combines the advantage of effectiveness and reliability with that of universality, being applicable to the detection of all cancerous tumors, regardless of their histological type, their location and their nature, original or metastatic.

This invention is also intended to propose a method of treatment for certain types of cancerous tumors, especially intracerebral tumors.

Another objective of this invention is the use, for diagnostic and/or treatment purposes, especially of cancer, of a specific glycoprotein, hyaluronectin.

This invention is in fact based on this twofold observation, first that hydraulic acid is present in all cancerous tumors, without exception, and second that is shown marked affinity for hyaluronectin, which is moreover capable of fixing a product such as a radioisotope, which is likely to have therapeutic action or be detected by external means of exploration, such as scintigraphy.

Hyaluronic acid is a glycosaminoglycan which constitutes a component of loose and inflammatory connective tissue, which is found in significant proportions in cancerous tissue, where it is associated with the extracellular matrix.

Hyaluronectin, a glycoprotein present in the brain and umbilical cord of humans and animals, has the advantageous characteristic of being of a markedly smaller size than the monoclonal antibodies, since it has a molecular mass of 68,000, so it is easily penetrated into the tissues.

Since hyaluronic acid is associated in significant proportions with the extracellular matrix of the cancerous tissues, it is easily accessible to hyaluronectin, which fixes itself on said tissues preferentially to the healthy connective tissue, in which its concentration is low or non-existent.

Marked by an appropriate radioisotope emitting gamma-rays such as indium, hyaluronectin can also permit location of the cancerous sites in an organism either by external imagery, by scintigraphy, or in preoperative spotting.

Furthermore, an appropriately charged dose of a radioisotope emitting beta-rays fixed on the hyaluronectin can allow for very effective treatment of certain radio-sensitive tumors, in particular intracerebral tumors.

Hyaluronectin used in the method of diagnosis and/or treatment according to the invention can be isolated from the brains of animals or the umbilical cords of humans, by passing an acid extract through a hyaluronic acid absorbent coupled with an aminohexyl-sepharose combination, followed by acid elution.

According to the invention's first presentation, applicable to cancer diagnosis, hyaluronectin is marked with the help of an element that is detectable by external means of exploration before being injected into the human body in the form of an aqueous solution.

The marking of hyaluronectin can be done using a radioisotope which is detectable by scintigraphy, but also using a paramagnetic element, such as gadolinium, detectable by nuclear magnetic resonance (NMR).

In the case of a radioisotope, any element that emits gammarays appropriate for radiodiagnosis can be used, such as indium-111, technetium 99, iodine 123 or iodine 131. This list should not be considered exhaustive.

Fixation of the selected element on hyaluronectin can be done by any known coupling method appropriate to the fixation of such an element on a protein molecule.

So, in the case of indium or technetium, a chelating agent, diethylenetriamine pentaacetic acid (DTPA), is used, so when coupling is performed with hyaluronectin, the free DTPA is eliminated by gel permeation chromatography before fixation of the indium or the technetium.

In the case of iodine, fixation can done using chloramine-T or an iodogenic substance.

Marking of hyaluronectin is done using the lowest quantities of radioactive element possible which are likely to be detected by standard means of exploration. This marking can thus be done such that the hyaluronectin carries a radioactive charge not to exceed 10 microcuries per microgram, and preferably between 1 and 5 microcuries per microgram.

According to the invention's second presentation, applicable to the treatment of cancer, hyaluronectin is charged with a radioactive isotope emitting beta-rays used in cancer radiotherapy, such as, for example, iodine 131.

In this second presentation, hyaluronectin serves as a vehicle for the therapy it presents to the various cancerous sites.

This method of treatment is particularly appropriate to the therapy of intracerebral tumors, which have the characteristic of not causing metastases and of being especially rich in accessible hyaluronic acid.

In this second presentation, the radioelement issuing beta-rays fixed on the hyaluronectin must be used in doses which allow a dose of several tens of grays to go to the tumor, in order of size of the doses delivered in external radiotherapy in the treatment of cancer.

The following example illustrates the method according to the invention applied to the diagnosis of cancer, it being understood that this example should not be considered as restrictive with regard to the invention.

EXAMPLE

Hyaluronectin is isolated from the brain of a lamb by running an acid extract through a hyaluronic acid absorbent coupled with AH-sepharose, followed by acid elution.

Next, coupling of the protein is carried out, determining the quantity of DPTA coupled on a portion that is marked in indium and performing thin-layer silica chromatography, with the free DTPA being eliminated on Sephadex G 100.

The activity of hyaluronectin (HN) is controlled by testing, on a section of tissue, its affinity for AH, then it is marked on indium 111, at the rate of 5 microcuries / mcg and injected into mice.

For this purpose we have selected DBA/2 mice carrying breast cancer transplanted from generation to generation, into which 6 mcg of marked HN has been injected. The mice were scintigraphed at Day 2, Day 3 and Day 4, and calculations of activity in the area of the tumor or the organs marked off on the images were determined at those same times, and the results attained are reported in the following table.

|  | Day 2 (3 cases) | Day 3 (4 cases) | Day 4 (5 cases) |
|---|---|---|---|
| Liver tumor | 0.66–0.96–0.64 | 0.86–0.89 0.82–0.50 | 0.58–0.70–0.60 0.47–0.60 |
| Head tumor | 3.42–4.59–3.08 | 4.88–4.74 3.70–3.50 | 2.56–4.67–3.38 3.40–2.95 |
| Abdominal tumor | 3.33–4.37–3.42 | 2.75–3.68 3.57–1.90 | 1.85–3.85–2.84 2.56–2.27 |

With the exception of the liver and kidneys, it was noted that fixation of HN in the tumor was always greater than its fixation in the other organs, with activity in the liver and kidneys corresponding to fixations not specific to the radiotracer (means of elimination).

Furthermore, activity counts on organs (liver, spleen, kidney, brain, muscle, lung, heart, blood) taken from the sacrified mice were done at Day 2, Day 4 and Day 6, and showed that radioactivity was not found in the brain, the heart or the lungs. The location indices for the protein marked in the tumor (Tu) relative to the blood were as follows:

|  | Day 2 (1 case) | Day 4 (2 cases) | Day 6 (3 cases) |
|---|---|---|---|
| Blood tumor | 6.5 | 11.7 5.1 | 11 8.7 11.8 |

The results, both from imagery and from biodistribution studies, showed that injected hyaluronectin fixes itself preferentially in the tumor, allowing for its detection and/or treatment.

The method of diagnosis and/or treatment according to the invention has the advantage, previously discussed, of permitting detection and location of all cancerous tumors, original or metastatic, regardless of their histological type, which constitutes considerable progress over known methods, and also permits effective treatment of certain types of tumors.

To this advantage we can add those benefits linked, on the one hand to the stability of hyaluronectin, which can be kept for several months at 4° C. and lasts for a few minutes at 100° C., and on the other hand, to the simplicity of its preparation, which does not raise any legal or ethical problems, since hyaluronectin can be isolated from the brains of animals or from umbilical cords.

In this respect, the use of a preparation made from a human umbilical cord would without a doubt eliminate any immunological reactions, which are always present with the monoclonal antibodies from mice.

This invention is not limited to the preceding description, and it is capable of undergoing modifications without overstepping the bounds of the invention.

It should especially be pointed out that an application outside the field of cancerology could be found, particularly in rheumatology, and in any case where there is a reaction of the connective stroma, bringing the accessability of hyaluronic acid to hyaluronectin.

We claim:

1. A diagnostic and/or therapeutic composition comprising an injectable solution of hyaluronectin, onto which a radioactive element is bound.

2. A composition according to claim 1, for the treatment of cancer, wherein the element bound on the hyaluronectin is a radioisotope emitting beta-rays.

3. A composition according to claim 2, wherein the radioisotope is iodine-131.

4. A composition according to claim 1, for the diagnosis of cancer wherein the radioactive element bound on the hyaluronectin is a radioisotope emitting gamma-rays detectable by scintigraphy.

5. A composition according to claim 2, wherein the radioisotope is selected from the group consisting of technetium-99, indium-111, iodine-123 and iodine-131.

6. A composition according to claim 2 wherein the radioisotope is used at the rate of 1 to 5 microcuries per microgram of hyaluronectin.

7. A composition according to claim 2, wherein the radioisotope is iodine-123 or iodine-131, bound on the hyaluronectin with an iodogenic agent.

8. A composition according to claim 2 wherein the radioisotope is indium-111 or technetium-99, bound on the hyaluronectin with a chelating agent.

9. A composition according to claim 8, wherein the chelating agent is diethylenetriamine pentaacetic acid.

* * * * *